US007722839B2

(12) United States Patent
Kuzyk

(10) Patent No.: US 7,722,839 B2
(45) Date of Patent: May 25, 2010

(54) APPARATUS AND METHOD FOR THAWING BIOLOGICAL MATERIALS

(75) Inventor: Roman Kuzyk, Hamilton Square, NJ (US)

(73) Assignee: Cytotherm, L.P., Hamilton Square, NJ (US)

(*) Notice: Subject to any disclaimer, the term of this patent is extended or adjusted under 35 U.S.C. 154(b) by 1980 days.

(21) Appl. No.: 10/268,610

(22) Filed: Oct. 10, 2002

(65) Prior Publication Data
US 2003/0082069 A1  May 1, 2003

Related U.S. Application Data

(60) Provisional application No. 60/328,545, filed on Oct. 11, 2001.

(51) Int. Cl.
| | |
|---|---|
| B01J 19/00 | (2006.01) |
| B01D 35/18 | (2006.01) |
| C12M 1/00 | (2006.01) |
| A61F 7/12 | (2006.01) |
| A61F 7/00 | (2006.01) |
| B65B 1/04 | (2006.01) |
| A61M 16/00 | (2006.01) |
| F24J 1/00 | (2006.01) |
| B30B 1/32 | (2006.01) |
| B65D 1/32 | (2006.01) |
| B65D 30/08 | (2006.01) |

(52) U.S. Cl. .................. 422/307; 422/255; 422/40; 210/175; 210/176; 210/177; 210/178; 435/303.1; 604/291; 604/113; 604/6.13; 392/470; 141/10; 128/203.28; 126/263.07; 100/269.04; 220/723; 220/721; 383/110

(58) Field of Classification Search .............. 422/255, 422/307, 40; 210/176–178, 175; 435/303.1; 604/291, 113, 6.13; 392/470; 141/10; 128/203.28; 126/263.07; 100/269.04; 220/723, 721; 383/110
See application file for complete search history.

(56) References Cited

U.S. PATENT DOCUMENTS 2,845,929 A * 8/1958 Strumia .................. 604/113

(Continued)

FOREIGN PATENT DOCUMENTS

| DE | 3741051 | 6/1989 |
|---|---|---|
| EP | 0318924 B1 | 11/1988 |

OTHER PUBLICATIONS

Thermogenesis, Plasma Thawers, "Simply the Best", 3 page advertisement.

(Continued)

*Primary Examiner*—Jill Warden
*Assistant Examiner*—Monzer R Chorbaji
(74) *Attorney, Agent, or Firm*—Donald R. Piper, Jr.; Dann Dorfman Herrell & Skillman, PC

(57) ABSTRACT

An apparatus and method are provided to rapidly thaw and heat frozen bags of biological materials, such as plasma. The apparatus has a hollow bladder having a flexible wall that is placed in contact with the bag. A circulation system draws fluid from a reservoir and fills the bladder with the fluid. The circulation system also drains fluid from the bladder. A heater in the reservoir heats the fluid before the fluid enters the bladder. As heated fluid flows through the bladder, heat is transferred through the bladder wall to the plasma bag to thaw the biological material. The bladder wall expands against the plasma bag as the bladder fills with fluid, and contracts from the plasma bag as the bladder is drained. The expansion and contraction of the bladder wall agitates the plasma bag and biological material to accelerate the thawing process.

35 Claims, 5 Drawing Sheets

U.S. PATENT DOCUMENTS

| | | | |
|---|---|---|---|
| 3,518,393 A | | 6/1970 | Besseling |
| 4,486,389 A | | 12/1984 | Darnell et al. |
| 4,539,005 A | * | 9/1985 | Greenblatt .................. 604/141 |
| 4,808,159 A | * | 2/1989 | Wilson ...................... 604/6.13 |
| 5,147,330 A | | 9/1992 | Kogel |
| 5,243,833 A | | 9/1993 | Coelho et al. |
| 5,282,264 A | * | 1/1994 | Reeves et al. ............... 392/382 |
| 5,403,279 A | * | 4/1995 | Inaba et al. ................... 604/65 |
| 5,645,194 A | * | 7/1997 | Tyner ......................... 222/147 |
| 5,733,263 A | * | 3/1998 | Wheatman .................. 604/141 |
| 5,743,878 A | * | 4/1998 | Ross et al. .................. 604/131 |
| 5,779,974 A | | 7/1998 | Kuzyk |
| 6,007,773 A | | 12/1999 | Kuzyk |
| 6,336,003 B1 | * | 1/2002 | Mitsunaga et al. .......... 392/470 |
| 6,748,164 B1 | * | 6/2004 | Kuzyk ......................... 392/443 |
| 6,824,528 B1 | * | 11/2004 | Faries et al. ................. 604/113 |

OTHER PUBLICATIONS

Photo-Therm, Plasma Thawing System—Cyto-Therm III T, 2 page advertisement.
Photo-Therm, Plasma Thawing System—Cyto-therm CT S, 2 page advertisement.
Labor Technik Barkey, plasmatherm, 4 page advertisement.
Barkey, TCS Infusion Warming Concepts, phasmaterm, 3 page web advertisement.
Transmed®, "New: Thawing of Stem Cell Preparations with Sahara-TSC", 1 page advertisement.

* cited by examiner

APPARATUS AND METHOD FOR THAWING BIOLOGICAL MATERIALS

RELATED APPLICATIONS

This application claims priority to U.S. Provisional Application No. 60/328,545, filed Oct. 11, 2001, which is hereby incorporated herein by reference.

FIELD OF THE INVENTION

The present invention relates to apparatuses for thawing biological materials, such as plasma, and more specifically to apparatuses that thaw biological materials by agitation and heat transfer.

BACKGROUND OF THE INVENTION

In the present state of the art, plasma and other biological materials are stored in a frozen state to preserve the materials for subsequent use in a patient. In many cases, it is desirable to thaw frozen biological materials rapidly. For example, frozen plasma must be thawed rapidly to be used in emergency situations. Rapid thawing is also desirable to limit the amount of time that thawed plasma sits in storage. Thawed plasma has a limited shelf life, and coagulant factors in thawed plasma can degrade in a relatively short amount of time. When thawing time is long, medical professionals often take many frozen units of plasma out of cold storage in advance of an operation, so that they have a large volume of thawed plasma available by the time the operation begins. This can result in wasted plasma if some of the units are not used. Rapid thawing allows medical professionals to order frozen units of plasma on an as-needed basis, reducing the potential for wasted plasma.

SUMMARY OF THE INVENTION

In a first aspect of the present invention, an apparatus is provided that rapidly thaws and heats biological materials, such as plasma, stored in an intravenous bag, packet or similar enclosure. The apparatus has a hollow bladder having a flexible wall that is placed in contact with the bag. A circulation system draws fluid from a reservoir and fills the bladder with the fluid. The circulation system also drains fluid from the bladder. A heater in the reservoir heats the fluid before the fluid enters the bladder. As heated fluid flows through the bladder, heat is transferred through the bladder wall to the plasma bag to thaw the biological material. The bladder wall expands against the plasma bag as the bladder fills with fluid, and contracts from the plasma bag as the bladder is drained. The expansion and contraction of the bladder wall agitates the plasma bag and biological material to accelerate the thawing process.

In a second aspect of the invention, a method is provided for thawing and heating biological materials in a bag. The bag is placed in contact with a hollow bladder having a flexible bladder wall. Fluid is heated to a desired temperature and pumped into the hollow bladder to expand the bladder wall against the bag and gently agitate the biological material. The heated fluid is maintained in the bladder to transfer heat through the bladder wall to the bag. Fluid is then withdrawn from the bladder to retract the bladder wall away from the bag.

BRIEF DESCRIPTION OF THE DRAWINGS

The foregoing summary as well as the following description will be better understood when read in conjunction with the figures in which.

DETAILED DESCRIPTION OF THE INVENTION

Referring to FIGS. 1-9 generally, and to FIGS. 1-4 in particular, an apparatus in accordance with the present invention is shown and designated generally as 20. The apparatus 20 is operable to thaw and/or heat up biological materials that are stored at low temperatures, including but not limited to human organs, tissue and plasma. For purposes of this description, the apparatus 20 will be described as it is used in thawing and heating frozen bags of plasma 21.

Figure 4:
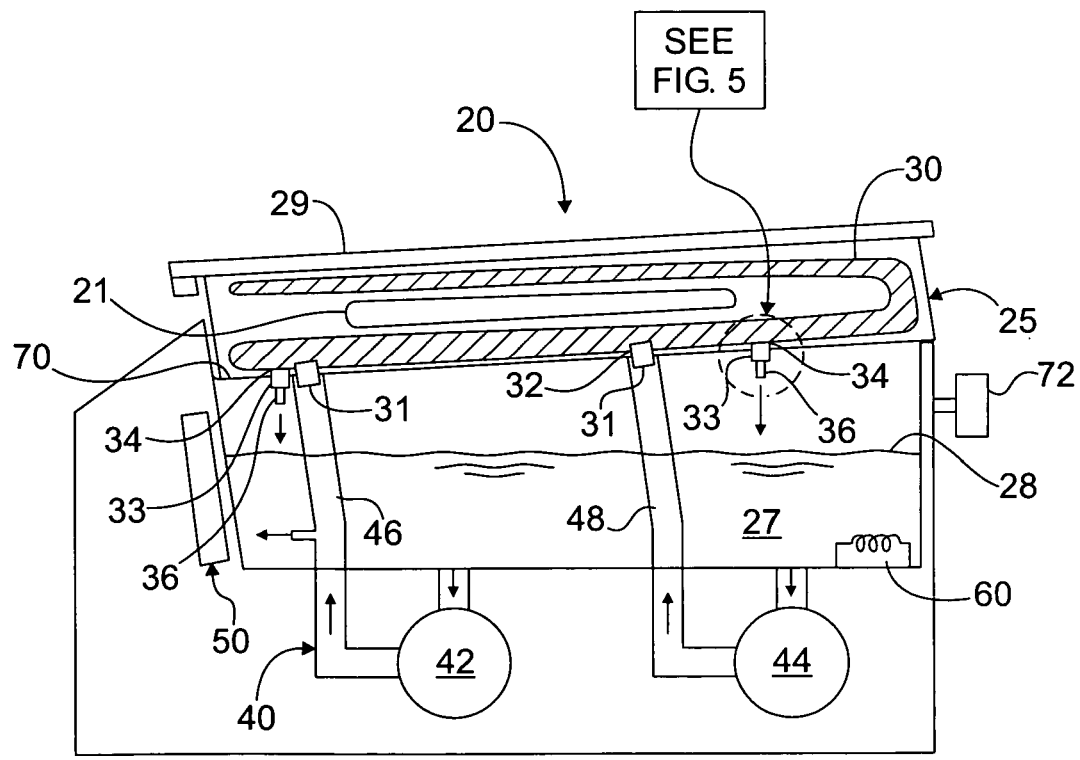
FIG. 4 is a sectional elevational view of the apparatus in FIG. 1.

The apparatus 20 has a generally rectangular tank 22. The tank 22 houses a reservoir 27 containing a fluid 28 and a system 40 that circulates fluid during the thawing process. The reservoir 27 contains a heater 60 in contact with the fluid 28, as shown in FIG. 4. The heater 60 is operable to heat the fluid 28 in the reservoir 27 to a desired temperature. A hollow bladder 30 having a flexible wall is disposed in the tank 22 in fluid connection with the circulation system 40. The bladder 30 may be placed in contact with the plasma bag 21 to be thawed. The circulation system 40 is operable to fill the bladder and exert pressure through the bladder wall against the plasma bag 21. The circulation system 40 also drains fluid from the bladder to release pressure from the plasma bag 21. The heated fluid 28 transfers heat to the biological material to assist in thawing the biological material.

Figure 3:
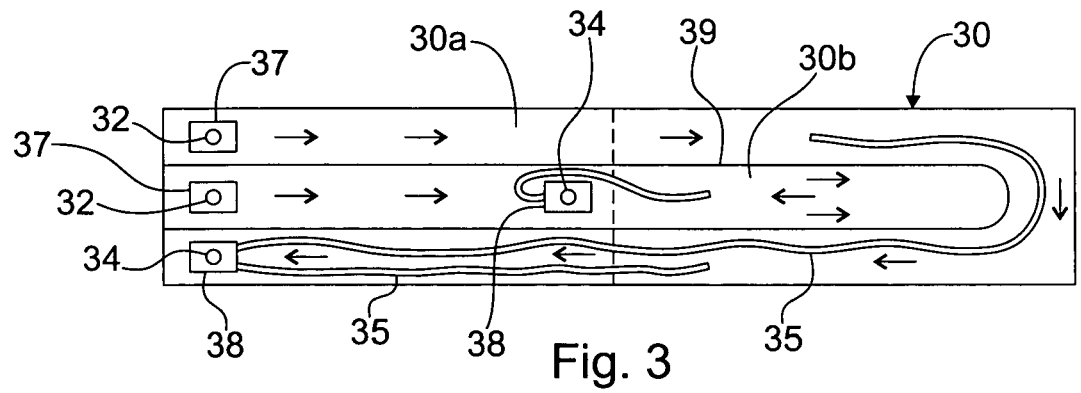
FIG. 3 is a top view of a bladder used in the apparatus in FIG. 1.

The apparatus 20 is configured to thaw the plasma bag 21 in a closed hydraulic system that keeps the bag dry. By keeping the plasma bag 21 dry, the sterility of the bag is maintained, and growth of bacteria is minimized. A number of bladder configurations and circulation systems may be used with the present invention. Referring to FIGS. 3-4, the bladder 30 is shown with two cells in fluid connection with the circulation system 40. The circulation system 40 is configured to pressurize and depressurize the cells intermittently so that the cells expand and contract in different cycles. As the cells expand and contract, the bladder wall agitates the biological material to accelerate thawing.

Figure 1:
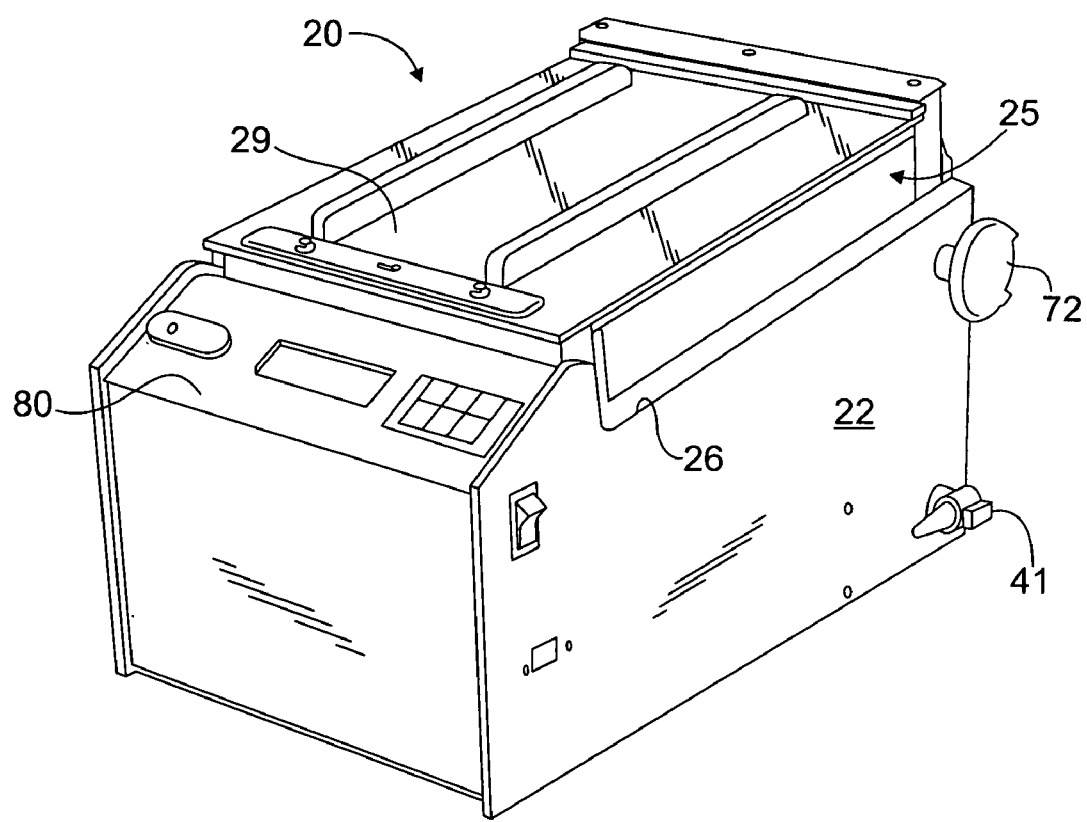
FIG. 1 is a perspective view of a thawing and heating apparatus in accordance with the present invention.
Figure 2:
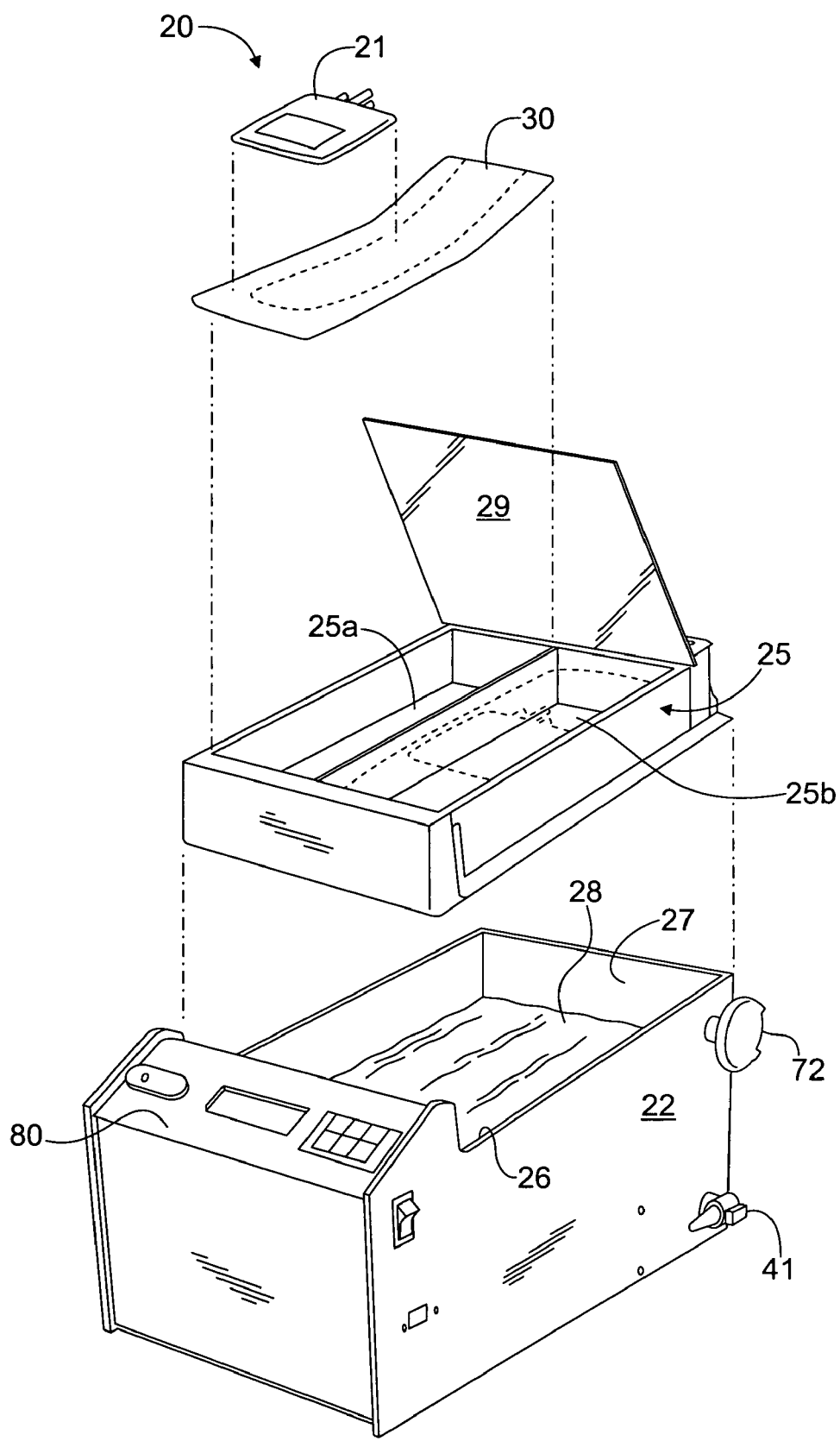
FIG. 2 is an exploded perspective view of the apparatus in FIG. 1.

Referring to FIGS. 1-2, the apparatus 20 will be described in greater detail. The tank 22 has an open top end and a receptacle 26 adapted to receive a generally rectangular tray or rack 25. The rack 25 is configured to rest in the receptacle 26 in the top end of the tank 22. The rack 25 supports the bladder 30 and the plasma bag 21 above the reservoir 27 and circulation system 40. The reservoir 27 in the tank 22 may be filled with fluid 28 through the open receptacle 26 when the rack 25 is removed. The tank 22 has a drain valve 41 operable to discharge fluid 28 from the reservoir 27.

A door or lid 29 is pivotally mounted on the top side of the rack 25. The lid 29 is pivotal between an open position, which permits access to the interior of the rack 25, and a closed position, which limits access to the interior of the rack. Preferably, the lid is formed of a transparent material, such as clear plastic or other rigid material. In addition, the bladder 30 is preferably formed of a transparent material, such as transparent polyethylene. In this way, the condition of the plasma bag 21 and bladder 30 can be observed through the lid during operation of the apparatus 20. The apparatus 20 may be operated by electric power, and is preferably configured to run on 120 VAC or 240 VAC.

The bladder 30 rests in the rack 25 and is placed in direct contact with the plasma bag 21 to be thawed. In the preferred embodiment, the bladder 30 is configured to lay flat in the rack 25 and fold more or less in half so as to wrap around the plasma bag 21, as shown in FIG. 4. In this way, the bladder 30 can agitate and transfer heat to both sides of the plasma bag 21 to efficiently thaw the plasma bag.

Referring to FIG. 3, the interior of the bladder 30 is divided into two cells 30A and 30B. The cells 30A and 30B are sealed from one another by a barrier 39 that prevents fluid in one cell from entering the other cell. Each of the cells 30A and 30B has an inlet block 37 and an outlet block 38. The inlet blocks each comprise an inlet port 32, and the outlet blocks 38 each comprise an outlet port 34. The inlet ports 32 and outlet ports 34 are connected to the circulation system 40 through a plurality of fittings that extend through the bottom of the rack 25. The fittings are configured to connect the bladders to the rack, and connect the rack to the circulation system. A number of fitting configurations may be used to connect the bladder 30, rack 25 and circulation system 40.

Air bubbles that form in the bladder 30 may attach to the interior wall and reduce the liquid surface area in contact with the interior wall. Since the fluid transfers heat through the wall by contacting the interior wall, trapped air can decrease the rate of heat transfer to the plasma. Large air pockets may reduce the rate of heat transfer and significantly impede the thawing process. Therefore, the bladder 30 preferably has a mechanism for removing air bubbles that form in the bladder.

In the preferred embodiment, the bladder 30 has air tubes that extend within the interior of the bladder and release air that accumulates in the bladder. Referring to FIG. 3, the outlet ports 34 of bladder cells 30A and 30B are shown connected to one or more small diameter air tubes 35. The air tubes 35 are configured to bleed air from the bladder 30 and discharge the air through the outlet ports 34 as fluid drains from the bladder. The first cell 30A preferably has two air tubes to capture air from different regions within the cell. Each air tube 35 has a small diameter inlet configured to draw air into the tube. The air tubes 35 are operable to release air from the bladder to improve the heat transfer efficiency of the bladder. It should be understood, however, that the present invention may be practiced successfully without the use of any mechanism to remove air from the interior of the bladder 30.

The inlet ends of the air tubes 35 are attached to the interior wall of the bladder so that the inlets are positioned toward the top of the bladder cell when the bladder is folded in the rack 25. In FIG. 3, the bladder 30 may be folded at the dashed line and placed in the rack so that the inlet and outlet blocks are positioned on the lower half of the bladder. The inlet ends of the air tubes 35 extend in the upper half of the bladder to capture air bubbles. The tubes may be attached to the interior wall by an adhesive tape, bonding or any other technique. In this way, the inlets are positioned near the top of the cells where air bubbles accumulate. Preferably, the bottom of the rack 25 is pitched or sloped, as shown in FIG. 4, so that one end of the bladder 30 is elevated above the opposite end of the bladder when the bladder rests on the rack. In this way, air bubbles that develop in the lower half of the bladder can migrate toward the elevated end of the bladder and rise to the upper half of the bladder to be captured by the air tubes 35.

Figure 5:
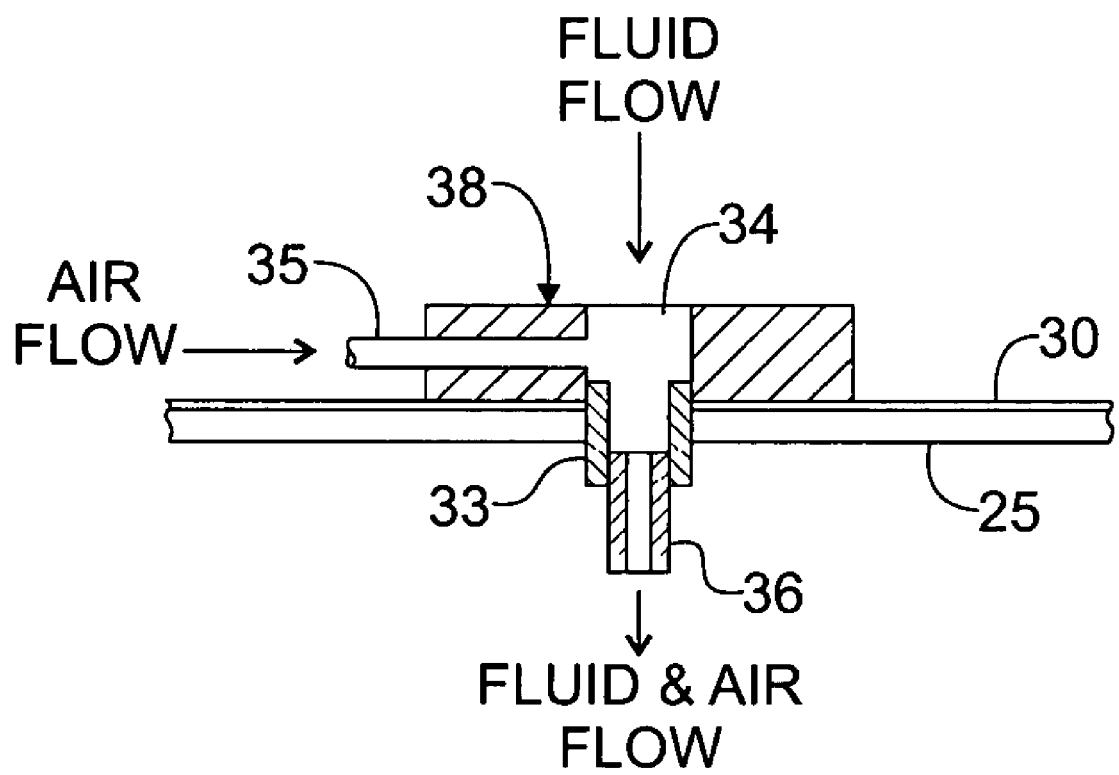
FIG. 5 is a fragmented sectional view of an outlet on a bladder used with the apparatus in FIG. 1.

The outlet end of each air tube 35 is connected to one of the outlet blocks to discharge air from the bladder. Each air tube 35 extends through one of the outlet blocks 38 and connects transversely with one of the outlet ports 34, as shown in FIG. 5. As fluid is discharged through the outlet port 34 past the end of the air tube 35, the passing flow exhibits low pressure at the outlet of the air tube. In contrast, the inlet end of the air tube 35 is subject to higher pressures in the bladder 30. As a result, a pressure differential is created in the air tube. The pressure differential creates suction pressure that draws air into the tube inlet and through the tube to the tube outlet, where it is discharged through the outlet port 34 of the bladder 30.

The circulation system 40 is configured to pump heated fluid 28 in a continuous cycle from the reservoir 27 to the bladder 30 and withdraw fluid from the bladder back to the reservoir. A number of hydraulic arrangements may be used in this invention. Referring to FIG. 4, the circulation system 40 has a first pump 42 configured to pump fluid 28 to the first cell 30A and a second pump 44 configured to pump fluid to the second cell 30B. The first and second pumps 42, 44 are connected to the bladder 30 by a pair of conduits 46, 48. Specifically, the pumps 42, 44 each have a discharge port that connects to one of the conduits 46, 48. The conduits 46, 48 extend from the pumps and connect to inlet fittings 31 that extend through the bottom of the rack 25. The inlet fittings 31 extend into the interior of the rack and are configured to mate with the inlet ports 32 on the bladder 30. The inlet fittings 31 may mate with the inlet ports using a variety of connections. For example, the inlet fittings may be inserted into the inlet ports and held by a friction fit connection.

The conduits 46, 48 connect to the inlet fittings 31 on the underside of the rack 25 when the rack is placed over the tank 22. The conduits 46, 48 may be formed of any suitable material. Preferably, the conduits are formed of flexible material, such as polyvinyl chloride tubing. In addition, the conduits 46, 48 preferably have a minimum of 12 inches of slack when the rack 25 is placed over the tank and connected with the conduits. In this way, the rack 25 can be lifted and maneuvered above the tank 22 without having to disconnect the conduits from the inlet fittings 31.

Referring to FIGS. 3-5, fluid 28 exits the bladder cells 30A, 30B through the outlet ports 34 and discharges back to the reservoir 27. Each outlet port 34 is connected to an outlet fitting 33 that extends through the bottom of the rack 25. Fluid is discharged from each outlet port 34 and through one of the outlet fittings 33 back to the reservoir 27. To expand the bladder cells 30A, 30B against the plasma bag, a positive fluid pressure is developed in the cells. Positive pressure is created by a flow constriction component 36 connected to each of the outlet fittings 33, as shown in FIG. 5. The flow constriction components 36 limit the discharge flow rate from the bladder cells. More specifically, the constriction components 36 limit the discharge flow from each bladder cell to a fraction of the flow rate that enters the bladder cell, creating a net positive flow of fluid that pressurizes each cell. When a pump is activated, the cell connected to that pump expands in response to pressure created by the net positive flow. When a pump deactivates, fluid flow into the cell halts, while fluid discharge through the outlet port 34 continues. As fluid in the cell drains through the outlet port, pressure in the cell is released, and the bladder wall contracts.

The first and second pumps 42, 44 are operable in different cycles to pressurize the cells 30A, 30B at different intervals. In particular, the pumps are operable to expand and contract the bladder cells at different intervals. The pumps 42, 44 are activated and deactivated by a controller 50. In the preferred embodiment, the controller 50 is configured to operate the pumps between a first mode and a second mode. In the first mode, the controller 50 activates the first pump 42 for a limited time period while the second pump 44 is deactivated. In the second mode, the controller 50 deactivates the first pump 42 and activates the second pump 44 for a limited time period. In this way, the first cell 30A expands while the second cell 30B contracts, and the second cell 30B expands while the first cell 30A contracts. The alternating expansion of cells 30A, 30B causes the bladder wall to oscillate as it contacts the plasma bag 21. This gently agitates the plasma bag to assist in thawing the plasma.

Figure 6:
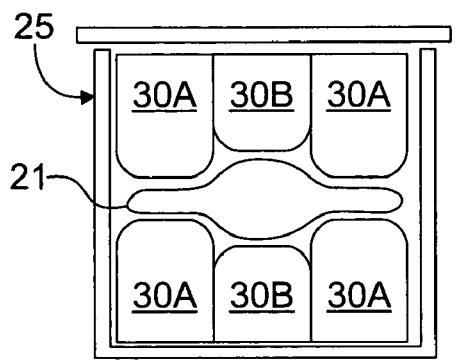
FIG. 6 is a sectional view of a portion of the thawing device in FIG. 1 during a first mode of operation.
Figure 7:
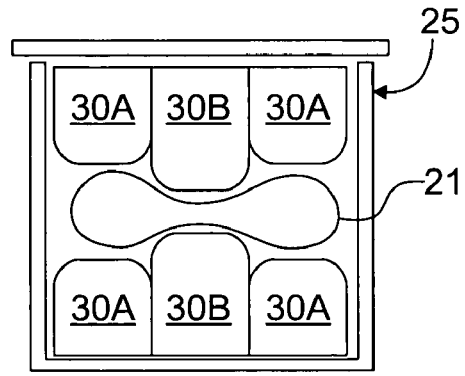
FIG. 7 is a sectional view of a portion of the thawing device in FIG. 1 during a second mode of operation.

Referring to FIGS. 6-7, the alternating expansion and contraction of cells 30A, 30B will be discussed in greater detail. Plasma bags are generally frozen in a solid state when in storage. As a result, most plasma bags are not in a fluid state when initially thawed and will not bend during agitation. For purposes of illustration, the plasma bag 21 is shown partially thawed in a fluid state. In this way, the effect of the alternating pump cycles may be visualized. As stated earlier, the bladder 30 is preferably folded over the plasma bag 21 in the apparatus 20 so that roughly one half of the bladder lies beneath the plasma bag and roughly one half of the bladder lies above the plasma bag. The bladder 30 is folded such that cell 30A is folded over itself and cell 30B is folded over itself. As such, cell 30A is aligned with the side portions of the plasma bag 21, and cell 30B is aligned with the middle portion of the plasma bag, as shown in FIGS. 6-7.

In FIG. 6, the apparatus is shown operating in the first mode in which the first pump 42 is activated and the second pump 44 is deactivated. In the first mode, the cell 30A is expanded and cell 30B is contracted. The expanded cell 30A exerts pressure on the side portions of the plasma bag 21. At the same time, contracted cell 30B exerts less pressure on the middle portion of the bag 21. This creates a pressure differential in the plasma bag 21, causing the plasma to shift from the sides of the bag toward the middle portion of the bag. In FIG. 7, the apparatus is shown operating in the second mode in which cell 30A is contracted and cell 30B is expanded. In the expanded state, cell 30B exerts pressure on the middle portion of the plasma bag 21 while cell 30A exerts less pressure on the side portions of the plasma bag. This creates a pressure differential in the plasma bag 21 that causes the plasma to shift from the middle portion of the bag toward the side portions of the bag. The circulation system 40 is preferably configured to alternate evenly between the first mode and the second mode. In this way, pressure is applied to side sections of the plasma bag 21 for the same duration as the middle portion. The controller 50 may comprise a cycle adjuster that controls the frequency in which the apparatus switches between the first mode to the second mode.

The apparatus 20 uses a closed hydraulic system to thaw plasma bags 21 in a dry environment, as stated earlier. It is desirable to maintain a dry environment in the rack 25 to minimize growth of bacteria and other contaminants. Leaks in the plasma bag 21 and/or bladder 30 will create moisture in the rack 25. Therefore, the apparatus preferably has a moisture detection system to alert operators of moisture or leaks that are present. As stated earlier, the bottom surface of the rack 25 is shown pitched or sloped at an angle. In FIG. 4, the bottom surface of the rack 25 is sloped toward the front of the apparatus 20. In the event of a leak, the sloped surface is configured to drain liquid from the plasma bag 21 or bladder 30 to the front of the rack 25. A moisture sensor 70 is disposed at the forward end of the rack 25 near the bottom surface to detect liquid in the rack. The sensor 70 may be wired to a signaling mechanism that alerts the operator of a possible leak. The signaling mechanism may be a lamp, such as an LED, an audible alarm or other signal mechanism.

The rack 25 may have a number of compartments that permit the apparatus to thaw multiple plasma bags at the same time. Referring to FIG. 2, the rack 25 is shown with two compartments 25A, 25B that are separated by a partition. The partition is configured to prevent any liquid in one compartment from entering the other compartment. In the event of a leak in one compartment, the plasma bag in the other compartment remains dry and does not need sterilization. The compartments 25A, 25B may be sized and configured in a number of ways to accommodate plasma bags and other items to be thawed. For example, where two compartments are used, each compartment may be sized to accommodate two 450 ml bags or one 1,000 ml bag.

The compartments 25A, 25B each have a pair of inlet fittings 31 and a pair of outlet fittings 33. As such, the two compartment rack 25 has a total of four inlet fittings. When two bladders are being used, with each bladder having two cells, it is necessary to split the flow from the two circulation pumps 42, 44 so that each pump can pump fluid 28 to both compartments 25A, 25B. This can be accomplished by connecting a T-shaped fitting to each conduit 46, 48 to split the flow from the respective pumps 42, 44.

A variety of controls may be provided for operating the circulation system 40 and heater. For example, a central control panel 80 may be mounted on the apparatus. The control panel may feature a start button to activate the heater and circulation pumps and a stop button to switch off the heater and circulation pumps. In addition, the control panel 80 may have a programmable timer configured to operate the circulation system 40 and heater 60 for a preset time. When the preset time expires, the timer switches off the circulation system 40 and heater 60. The apparatus may also have a thermostat that monitors and maintains the temperature of fluid in the reservoir to a suitable temperature for thawing the plasma bag. In the preferred embodiment, a programmable thermostat is provided to regulate the temperature of fluid to a preset temperature. For example, the thermostat may be set to 37° C. (98.6° F.) to heat a quantity of plasma to a temperature compatible with a patient's body temperature. The thermostat may be wired to the heater and switch the heater on when the bath falls below the desired temperature, or switch the heater off when the fluid temperature exceeds the desired temperature. A digital or LCD readout may be provided to display operating conditions in the apparatus, including elapsed heating time, temperature in the fluid reservoir, or the presence of a leak in the rack.

When the amount of fluid in the reservoir is low, the apparatus will not operate properly. Preferably, the apparatus has a horizontal fill line marked or embossed in the interior of the tank. The fill line is positioned so that an operator can visually determine how much fluid to deposit in the tank. In addition, the apparatus preferably has liquid level sensor configured to contact the fluid in the reservoir when the reservoir is filled to a predetermined level. The sensor is connected to an alarm that activates when the fluid level drops below the predetermined level in the reservoir. The alarm may include a light, audible sound or other appropriate signal to alert the operator. The sensor may also be configured to switch off the heater and circulation pumps when the alarm is activated.

The lid 29 preferably has a latch or other locking mechanism that secures the lid in the closed position and limits access to the interior of the rack 25 during operation of the apparatus 20. The lid 29 may also be equipped with an interlock mechanism that prevents operation of the apparatus if the lid is not closed. A number of components can be used to form the interlock. For example, a magnet may be mounted on the lid 29 and linked to a sensor in the tank 22. Specifically, the sensor is positioned in the tank 22 to detect the magnetic field when the lid is in the closed position. The sensor is configured to interlock the apparatus when the magnetic field is not detected. In this way, the circulation system 40 and heater 60 can not be started when the lid 29 is open. Moreover, the circulation system 40 and heater 60 can be automatically shut off if the lid 29 is opened during operation of the apparatus 20.

The apparatus 20 may be used to heat materials to various temperatures for different applications. As described earlier, the apparatus 20 may be programmed to heat plasma to a temperature of 37° C., which is compatible with human body temperature. Alternatively, the apparatus 20 may be used to heat and maintain materials to temperatures that are below ambient temperature. For example, the apparatus 20 may be used to maintain the temperature of materials at 6° C., well below room temperature. The tank 22 is connected to a separate chilling device. Fluid in the reservoir is pumped out of the tank 22 and circulated through the chilling device to lower the fluid temperature to 1° C. The chilled fluid is then cycled back to the reservoir where the heater 60 raises the temperature of the fluid to 6° C. The fluid in the reservoir is maintained at 6° C. by recirculating a portion of the fluid bath through the chilling device and heating the return flow in the reservoir so that the bath remains at 6° C.

The fluid reservoir 27 is exposed to air that enters and leaves the tank 22. As fluid 28 is pumped out of the reservoir 27, the displacement of fluid causes air to enter the reservoir area. Dust or other contaminants in the air can contaminate the fluid 28 and build up in the reservoir 27. Therefore, the apparatus 20 preferably has an air filter 72 that filters air entering the reservoir 27 from outside the tank 22. For example, the apparatus 20 may include a 0.3 micron filter 72 that captures dusts and other contaminants in the surrounding air. By filtering air that enters the tank 22, accumulation of dust or contaminants in the reservoir is reduced. In addition, the air filter 72 decreases the need for periodic cleaning and sterilization of the reservoir 27.

Figure 8:
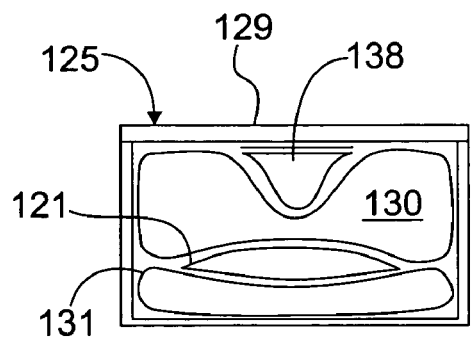
FIG. 8 is a sectional view of an alternate embodiment of the invention during a first mode of operation.
Figure 9:
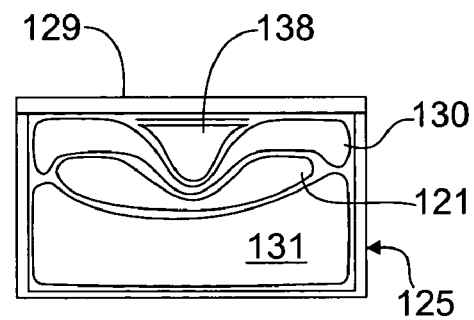
FIG. 9 is a sectional view of an alternate embodiment of the invention during a second mode of operation.

Thus far, one bladder configuration has been described in detail and illustrated. The present invention is intended to work with a number of bladder configurations, and the configuration described thus far is not the only configuration contemplated. Referring to FIGS. 8-9, a second embodiment of the invention is shown using upper and lower bladders 130, 131 in a rack 125. The upper and lower bladders 130, 131 are placed above and below a plasma bag 121, respectively. The rack 125 has a lid 129 with a rigid projection or hub 138 that extends inwardly and bears against the upper bladder 130 when the lid is closed. The bladders 130, 131 are each connected to separate circulation pumps that are operable to expand and contract the bladders at different intervals. As in the previous embodiment, the pumps operate in a first mode and a second mode, and each bladder drains fluid to a fluid reservoir in the apparatus.

In the first mode, a first pump fills the upper bladder 130 with fluid while the lower bladder 131 is drained. In the second mode, a second pump fills the lower bladder 131 while the upper bladder 130 is drained. When the upper bladder is filled and pressurized, the plasma bag 121 is compressed downwardly against the lower bladder 131, as shown in FIG. 8. When the lower bladder 131 is pressurized, the plasma bag is compressed upwardly against the upper bladder 130, as shown in FIG. 9. During the second mode of operation, the upper bladder 130 exerts less pressure on the plasma bag than the lower bladder 131 and therefore yields in response to the pressure exerted by the lower bladder 131. As the upper bladder 130 and plasma bag are compressed upwardly, the upper bladder and plasma bag bend upwardly against the curved hub. As a result, operation of the pumps between the first and second modes bends the plasma bag upwardly and downwardly in a continuous cycle to agitate the plasma.

Operation of the apparatus 20 will now be described with reference to the first embodiment. The tank 22 is placed on a level surface, and the rack is disconnected from any conduits or tubing beneath the rack. The rack 25 is then removed from the receptacle on the top of the tank so that the top of the tank is open and the reservoir 27 is exposed. The reservoir 27 is filled with tap water, deionized water or other appropriate fluid. If deionized water is used, a source of ions, such as salt, should be added to the water to make the water conductive. In this way, the water level sensor in the reservoir 27 can monitor the water level and detect when the water level is low. If desired, a chemical additive to limit algae growth may also be added to the fluid 28.

Once the reservoir 27 is filled with fluid 28, the rack is held above the tank 22, and the conduits 46, 48 are connected to the inlet fittings 31 on the underside of the rack 25. The rack 25 is then lowered into the receptacle on the tank 22. One or more bladders 30 are then connected to the rack. Specifically, a bladder 30 is placed in each of the compartments. The inlet fittings 31 are connected to the inlet ports 32 on the bladders 30, and the outlet fittings 33 are connected to the outlet ports on the bladders. The lid 29 on the rack 25 is pivoted to the closed position and latched. The tank is then connected to a power source, and the apparatus 20 is switched on. The heater 60 is activated to heat the fluid 28 in the reservoir 27 to the desired temperature. One or both of the circulation pumps 42, 44 are activated to circulate the fluid in the reservoir.

Once the desired temperature in the fluid reservoir 27 is reached, the heater 60 is switched off, and the lid 29 on the rack 25 is unlatched and opened. One or more plasma bags 21 are taken out of storage and placed on the bladders in the rack 25. The bladders 30 are preferably folded around the plasma bags 21 so that each bladder is wrapped around a plasma bag and contacts top and bottom sides of the plasma bag. The lid 29 on the rack 25 is then pivoted to the closed position and latched. Both circulation pumps 42, 44 circulate the fluid through the bladder to begin thawing the plasma bags. If a programmable timer is provided, the timer is adjusted to set a desired thawing time. The circulation system 40 continues operate until the programmed time expires.

The controller 50 regulates the operation of the circulation pumps 42, 44 so that the bladder cells expand and contract at different intervals. The first circulation pump 42 fills the first cell 30A of a bladder with heated fluid. A portion of the incoming flow exits through the outlet port 34 of the first cell 30A and discharges back to the reservoir 27 through a constriction component 36. The incoming flow rate in the first cell 30A is greater than the discharge flow rate, creating a net positive flow of fluid 28 in the cell. As a result, the first cell 30A fills to capacity with fluid 28 and becomes pressurized.

As the first cell 30A fills with fluid 28, the bladder wall surrounding the first cell expands against the plasma bag 21. The controller 50 then deactivates the first circulation pump 42 and activates the second circulation pump 44. Fluid in the first cell 30A continues to discharge through the outlet port 34 to the reservoir 27, releasing pressure in the first cell. As pressure in the first cell 30A is released, the bladder wall retracts, releasing pressure from the plasma bag 21.

Once the second circulation pump 44 is activated, the second bladder cell 30B fills with fluid 28 so that the bladder wall surrounding the second cell expands against the plasma bag 21. A portion of the incoming flow exits through the outlet port 34 of the second cell and discharges back to the reservoir 27 through a constriction component 36. The incoming flow rate in the second cell 30B is greater than the discharge flow rate, creating a net positive flow of fluid in the cell. As a result, the second cell 30B fills with fluid and becomes pressurized. As the second cell 30B fills with fluid, the bladder wall surrounding the second cell expands against the plasma bag 21, similar to the first cell 30A. The controller 50 deactivates the second circulation pump 44 after the second cell 30B is filled. Fluid in the second cell 30B continues to discharge through the outlet port 34, releasing pressure in the second cell. As pressure in the second cell 30B is released, the bladder wall retracts, releasing pressure from the plasma bag 21. The controller 50 activates the first circulation pump 42, and the cycle is repeated with the first bladder cell 30A.

The alternating expansion and contraction of the bladder cells 30A, 30B causes the bladder wall to massage the plasma bag 21. As a result, the moving bladder gently agitates the plasma bag 21 to assist in thawing the plasma. In the preferred embodiment, the thawing process can be observed by looking through the transparent lid 29 and transparent bladders. The circulation pumps 42, 44 operate until the preset time expires on the control panel. As time expires, the circulation system 40 shuts off. If the plasma bag 21 still appears partially frozen, the circulation system 40 may be restarted to thaw the plasma for an additional amount of time. The thawing cycle may be terminated manually before the programmed time expires by pressing a stop button on the control panel. Once the pumps 42, 44 are stopped, fluid in the bladders drains back to the reservoir 27 and pressure is released from the plasma bags 21. In addition, if the heater 60 is running, the heater is shut off.

The terms and expressions which have been employed are used as terms of description and not of limitation. There is no intention in the use of such terms and expressions of excluding any equivalents of the features shown and described or portions thereof. It is recognized, therefore, that various modifications are possible within the scope and spirit of the invention. Accordingly, the invention incorporates variations that fall within the scope of the following claims.

The invention claimed is:

1. An apparatus for thawing and heating biological material contained in a bag, said apparatus comprising:
   A. a multi-chambered bladder having a flexible wall for engagement with the bag;
   B. a reservoir containing a fluid;
   C. a circulation system operably communicating with the reservoir to fill the bladder with the fluid from the reservoir and expand the bladder wall and effect movement of the bag, and operable to withdraw the fluid from the bladder for circulating into the reservoir thereby causing the bladder wall to contract and effect movement of the bag, wherein said circulation system moves the fluid in such a manner that one chamber of the bladder may fill or empty fluid independently of another chamber; and
   D. a heater operable to heat the fluid within the reservoir, wherein the expansion and contraction of the bladder wall in response to operation of the circulation system agitates the bag and the biological material, and wherein the bladder wall is thermally conductive to transfer heat from the heated fluid in the bladder to the bag of the biological material.

2. The apparatus of claim 1, wherein the bladder comprises:
   A. an outlet through which fluid exits the bladder; and
   B. a hollow tube extending within the bladder, said hollow tube having a first open end communicating with the outlet and a second open end disposed within the bladder,
   wherein, the communication between the outlet and the first open end of the tube is configured to permit a suction pressure to be formed at the first open end of the tube as fluid exits through the outlet, said suction pressure being operable to draw a quantity of gas from the interior of the bladder through the second open end of the tube and discharge said quantity of gas through the first open end of the tube and through the outlet.

3. The apparatus of claim 1, wherein the bladder comprises a first cell having an inlet and an outlet communicating with the circulation system, and a second cell having an inlet and an outlet communicating with the circulation system, said first and second cells being sealed from one another and configured to expand and contract in response to operation of the circulation system.

4. The apparatus of claim 3, wherein the circulation system comprises a first pump connected with the first cell, and a second pump connected with the second cell, said first pump and second pump being operable to expand the first and second cells respectively.

5. The apparatus of claim 4, comprising a controller configured to activate the first pump during a period of time that the second pump is deactivated and activate the second pump during a period of time that the first pump is deactivated.

6. The apparatus of claim 5, wherein the controller comprises a cycle adjuster to control the frequency of operation of the first pump and the second pump.

7. The apparatus of claim 5, comprising a timer that limits operation of the heater and circulation system to a time duration.

8. The apparatus of claim 1, comprising a thermostat operable to measure the temperature of the fluid in the reservoir and regulate the heater to maintain a desired temperature in the fluid.

9. The apparatus of claim 8 wherein the heater is responsive to the thermostat to maintain the desired temperature between 6° C.-38° C.

10. The apparatus of claim 1, wherein the fluid is water.

11. The apparatus of claim 1 comprising a rack to support the bag and a tank that houses the reservoir and at least a portion of the circulation system.

12. The apparatus of claim 11, wherein the rack comprises a sensor operable to detect a fluid leak from the bladder or bag.

13. An apparatus for thawing and heating biological material in a bag, said apparatus comprising:
   A. a bladder having a flexible wall for engagement with the bag;
   B. a reservoir containing a fluid;
   C. a circulation system operably communicating with the reservoir to convey fluid from the reservoir to the bladder and withdraw the fluid from the bladder for circulation to the reservoir;

D. a first cell in the bladder having an inlet and an outlet communicating with the circulation system and configured to expand and contract in response to operation of the circulation system;

E. a second cell in the bladder having an inlet and an outlet communicating with the circulation system and configured to expand and contract in response to operation of the circulation system; and F. a heater operable to heat the fluid within the reservoir, wherein the inlets are configured to pass fluid from the reservoir into the bladder to expand the first and second cells, and the outlets are configured to pass fluid out of the bladder to the reservoir to contract the first and second cells, said expansion and contraction of the first and second cells being operable to agitate the bag, and wherein the passage of fluid through the bladder is operable to transfer heat to the bag of the biological material.

14. The apparatus of claim 13, wherein each cell comprises a hollow tube extending within the cell, said hollow tube having a first open end communicating with the outlet of the cell and a second open end disposed within the cell, wherein the communication between the outlet and the first open end of the tube is configured to permit a suction pressure to be formed at the first open end of the tube as fluid passes through the outlet, said suction pressure being operable to draw a quantity of gas formed in the interior of the bladder through the second open end of the tube and discharge said quantity of gas through the first open end of the tube and through the outlet.

15. The apparatus of claim 13, wherein the circulation system comprises:
  A. a first pump connected with the inlet of the first cell; and
  B. a second pump connected with the inlet of the second cell.

16. The apparatus of claim 15, comprising a controller configured to activate the first pump during a period of time that the second pump is deactivated and operate the second pump during a period of time that the first pump is deactivated.

17. The apparatus of claim 16, wherein the controller comprises a cycle adjuster to control the frequency of operation of the first pump and the second pump.

18. The apparatus of claim 13, comprising a timer that limits operation of the heater and circulation system to a time duration.

19. The apparatus of claim 13, comprising a thermostat operable to measure the temperature of the fluid in the reservoir and regulate the heater to maintain a desired temperature in the fluid.

20. The apparatus of claim 19 wherein the desired temperature is between 6° C.-38° C.

21. The apparatus of claim 13, wherein the fluid is water.

22. The apparatus of claim 13 comprising a tank having a lower section that houses the reservoir and circulation system, and an upper section that houses the bladder for engaging the bag.

23. The apparatus of claim 22, wherein the upper section comprises a sensor operable to detect a fluid leak from the bladder or the bag.

24. A method for thawing and heating a biological material in a bag, comprising the steps of:
  A. heating a fluid to a desired temperature;
  B. placing the bag containing the biological material in contact with a bladder having a flexible wall, and at least a first and second cell;
  C. pumping the heated fluid into the bladder to expand the bladder wall to agitate the biological material;
  D. maintaining the heated fluid in the bladder to transfer heat through the bladder wall to the bag; and
  E. withdrawing the heated fluid from the bladder to contract the bladder wall and agitate the biological material.

25. The method of claim 24 wherein the steps of pumping the heated fluid to the bladder and withdrawing the fluid from the bladder comprise pumping fluid to the first cell to pressurize and expand the first cell while draining fluid from the second cell, and then pumping fluid to the second cell to pressurize and expand the second cell while draining fluid from the first cell.

26. The method of claim 24 wherein the step of heating a fluid to a desired temperature includes heating the fluid to a desired temperature of between 6° C.-38° C.

27. The method of claim 24 comprising the step of removing a quantity of gas formed in the interior of the bladder.

28. An apparatus for thawing and heating biological material contained in a bag, said apparatus comprising:
  A. a bladder having a flexible wall for engagement with the bag;
  B. a reservoir containing a fluid;
  C. a circulation system operably communicating with the reservoir to fill the bladder with the fluid from the reservoir and expand the bladder wall and effect movement of the bag, and operable to withdraw the fluid from the bladder for circulating into the reservoir thereby causing the bladder wall to contract and effect movement of the bag;
  D. a heater operable to heat the fluid within the reservoir; and
  E. at least one flexible tube extending into the bladder to permit gas to flow through the tube,
  wherein the expansion and contraction of the bladder wall in response to operation of the circulation system agitates the bag and the biological material, and wherein the bladder wall is thermally conductive to transfer heat from the heated fluid in the bladder to the bag of the biological material.

29. The apparatus of claim 28, wherein the bladder has an outlet and an interior and wherein the tube has one end communicating with the outlet from the bladder and the other end communicating with the interior of the bladder at a position relatively higher than the outlet to permit gas to flow through the tube.

30. The apparatus of claim 28, wherein the flexible tube extends from a port on the bladder within an interior of the bladder so that any pressure differential between the ends of the tube permits gas to flow through the tube in communication with the port.

31. The apparatus of claim 28, wherein the bladder comprises a multi-chamber bladder and wherein the flexible tube includes a tube for each chamber.

32. An apparatus for thawing and heating biological material contained in a bag, said apparatus comprising:
  A. a bladder having a flexible wall for engagement with the bag and at least one inlet and multiple outlets;
  B. a reservoir containing a fluid;
  C. a circulation system operable to fill the bladder with the fluid from the reservoir through the inlet and expand the bladder wall and effect movement of the bag, and operable to withdraw the fluid from the bladder for circulation into the reservoir through the outlets thereby causing the bladder wall to contract and effect movement of the bag of biological material; and
  D. a heater operable to heat the fluid within the reservoir, wherein the expansion and contraction of the bladder wall in response to operation of the circulation system agitates the bag and the biological material, and wherein the bladder wall is thermally conductive to transfer heat from the heated fluid in the bladder to the bag of the biological material.

33. The apparatus of claim 32 comprising multiple inlets.

34. An apparatus for thawing and heating biological material contained in a bag, said apparatus comprising:

A. a bladder having a flexible wall for engagement with the bag and multiple inlets and at least one outlet;

B. a reservoir containing a fluid;

C. a circulation system operable to fill the bladder with the fluid from the reservoir through the inlet and expand the bladder wall and effect movement of the bag, and operable to withdraw the fluid from the bladder for circulation into the reservoir through the outlets thereby causing the bladder wall to contract and effect movement of the bag of biological material; and D. a heater operable to heat the fluid within the reservoir, wherein the expansion and contraction of the bladder wall in response to operation of the circulation system agitates the bag and the biological material, and wherein the bladder wall is thermally conductive to transfer heat from the heated fluid in the bladder to the bag of the biological material.

35. The apparatus of claim 34 comprising multiple outlets.

* * * * *